United States Patent [19]

Flanagan

[11] Patent Number: 4,743,275

[45] Date of Patent: May 10, 1988

[54] ELECTRON FIELD GENERATOR

[76] Inventor: G. Patrick Flanagan, P.O. Box 2285, Sedona, Ariz. 86336

[21] Appl. No.: 899,713

[22] Filed: Aug. 25, 1986

[51] Int. Cl.$^4$ .................... B03C 3/12; B03C 3/41
[52] U.S. Cl. ........................................... 55/2; 55/123; 55/138; 55/150; 361/226; 361/230
[58] Field of Search ................ 55/2, 123, 146, 150, 55/155, 138; 361/225, 226, 230, 231

[56] References Cited

U.S. PATENT DOCUMENTS

| | | | |
|---|---|---|---|
| 2,085,735 | 7/1937 | Brion et al. | 55/150 X |
| 2,086,063 | 7/1937 | Brion et al. | 55/123 |
| 2,239,694 | 4/1941 | Bennett | 361/230 X |
| 2,958,393 | 11/1960 | Lueder | 55/155 |
| 3,403,252 | 9/1968 | Nagy | 361/231 |
| 3,417,302 | 12/1968 | Lueder | 55/2 X |
| 3,789,278 | 1/1974 | Bingham et al. | 361/230 X |
| 3,970,905 | 7/1976 | Itoh et al. | 55/146 X |
| 4,037,268 | 7/1977 | Gallagher | 55/150 X |
| 4,096,544 | 6/1978 | Ignatjev | 361/231 |
| 4,391,773 | 7/1983 | Flanagan | 55/2 X |

Primary Examiner—Kathleen J. Prunner
Attorney, Agent, or Firm—Edmond T. Patnaude

[57] ABSTRACT

A negative field generator has a dielectric slab which is doped with discrete conductive members and sandwiched between a pair of electrodes. The electrodes and the dielectric member are encapsulated in a dielectric material and the electrodes are connected across a source of high frequency high A.C. voltage.

13 Claims, 1 Drawing Sheet

ELECTRON FIELD GENERATOR

The present invention relates in general to a new and improved device and method for generating a negative electric field of sufficient intensity to purify air, and it also relates to a novel method of enhancing the field strength of an electric field generator.

BACKGROUND OF THE INVENTION

In U.S. Pat. No. 4,391,773 there is decribed a negative field generator having utility in the purification of air. The generator which is described in that patent includes a field emitting device in the form of a flat solid dielectric material on the opposite faces of which a pair of electrodes are respectively disposed. When a high frequency, high voltage source is connected across the electrodes, a high intensity, high frequency negative field is developed in the space surrounding the field emitting device, and this negative field causes airborne solids to precipitate out of the surrounding air.

SUMMARY OF THE INVENTION

Briefly, in accordance with the teachings of the present invention the strength of the negative field generated by the above-described prior art field emitter is advantageously affected by altering the composition of the dielectric. I have found that if the dielectric material is doped with conductive or semiconductive particles the strength of the field produced externally of the field emiter is greatly increased.

In accordance with another aspect of the present invention, a plurality of the novel field emitters of the present invention can be strategically located in a room or other area to purify the air in the room without the need for auxiliary means for circulating the air in the room past the field emitters. Also, a plurality of the novel field emitters can be stacked on one another and connected in series across the high frequency, high voltage source to increase the strength of the negative field developed around the emitter.

GENERAL DESCRIPTION OF THE DRAWINGS

The present invention will be better understood by a reading of the following detailed description taken in connection with the accompanying drawing wherein.

DETAILED DESCRIPTION OF A PREFERRED EMBODIMENT

Figure 1:
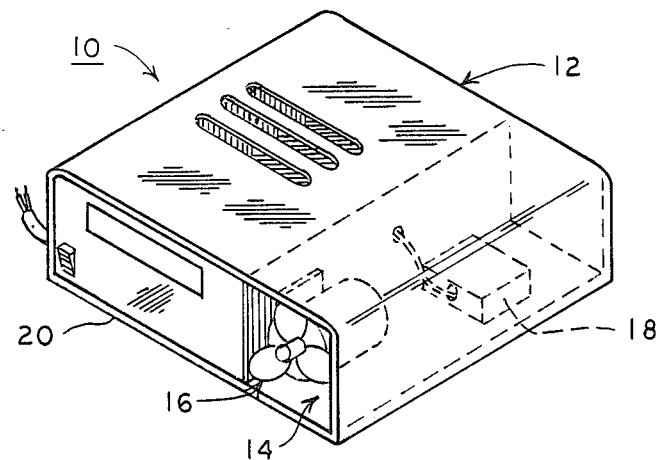
FIG. 1 is a perspective view of an air purifier embodying the novel negative field generator of the present invention.

Referring to FIG. 1, there is shown a metal housing or cabinet 12 in which is mounted an electronic control unit including a high voltage, high frequency power supply having a voltage of at least 5000 volts and a frequency of at least 20 kiloHertz. A passageway or tunnel 14 connected to the power supply is located at one side of the cabinet and is surrounded by the metal cabinet, which itself is connected to ground. A low velocity electric fan 16 is mounted in the tunnel near the front end thereof to cause the ambient air to flow into the front end and out the back end of the tunnel. A negative electric field emitter 18 is mounted to the floor 20 of the cabinet 12 within the tunnel 14 so that the air flowing through the tunnel passes through the negative electric field which surrounds the field emitter 18 which is confined by the grounded metal walls of the tunnel. As the air flows through the tunnel 14 it is thus treated by the high frequency, high energy negative field which surrounds the field emitter 18.

As discussed above, solid matter carried by the air is precipitated by the negative field and if desired, a porous filter (not shown) may be placed over the rear end of the tunnel to collect the precipitated particles before they leave the tunnel. Otherwise, as tests have shown, the precipitated particles will drop to the floor in the vicinity of the device 10.

Another use of the device 10 is in the conversion of carbon monoxide to carbon dioxide as carbon monoxide gas is passed through the tunnel 14. Also the electric charge on material located a substantial distance from the device 10 has been altered by the air exiting the tunnel 14. In this latter case the use of the device 10 in a pillow manufacturing plant caused pieces of foam filler which had previously clung to the walls and ceilings of the area to fall to the floor where they were then easily swept up. The device 10 also works well as a deodorizer.

Figure 2:
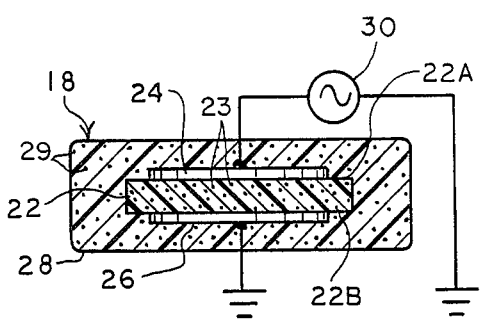
FIG. 2 is a cross-sectional view of a negative field generator embodying a novel field emitter constructed in accordance with the teachings of the present invention.

Referring to FIG. 2, the field emitter 18 may be seen to comprise a slab or sheet 22 of a solid dielectric material such as glass, paraffin, acrylic, epoxy or other suitable dielectric in which a plurality of small particles or granules 23 of conductive or semiconductive material are dispersed. A pair of planar electrodes 24 and 26 are mounted to the opposite faces 22A and 22B of the member 22 to form a capacitor which may be encapsulated in an insulator 28. The member 22 is square when viewed from the top as are the electrodes 24 and 26, but these members may, if desired, be circular or of some other suitable shape. The corresponding dimensions of the dielectric member are greater than those of the electrodes 24 and 26. The insulator 28 is also a solid dielectric material such as glass, paraffin, acrylic, epoxy or other suitable dielectric and may be doped so as to include conductive or semiconductive particles or granules 29 dispersed therein.

As shown, the electrode 24 is connected to one terminal of a high voltage, high frequency source of electric energy 30, and the electrode 26 is connected via ground to the other terminal of the energy source 30. The voltage applied across the emitter has a frequency of at least 20 kiloHertz and a voltage of at least 5000 volts RMS.

The reason why the field strength is increased by the presence of conductive particles in the dielectric material is not fully understood. However, comparative tests have proven that the electric field is strengthened and significantly improved air purification is achieved when such materials are dispersed in the dielectric, and it is believed that the work function of the dielectric is altered by the added material and this results in the increased emission from the device.

Figure 3:
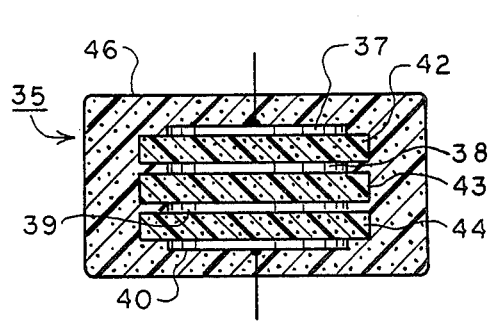
FIG. 3 is a cross-sectional view of another field emitter embodying the present invention.

Referring to FIG. 3, there is shown a negative electric field emitter 35 which comprises a plurality of planar metallic electrodes 37, 38, 39 and 40 separated by a plurality of flat dielectric members 42, 43 and 44. The electrodes and the dielectric members are encapsulated in an insulating material 46. Conductive leads extend from the electrodes 37 and 40 through the insulating material 46 for connection of the field emitter 35 to a high frequency, high voltage source to develop a generally toroidal electric field around the field emitter 35.

Figure 4:
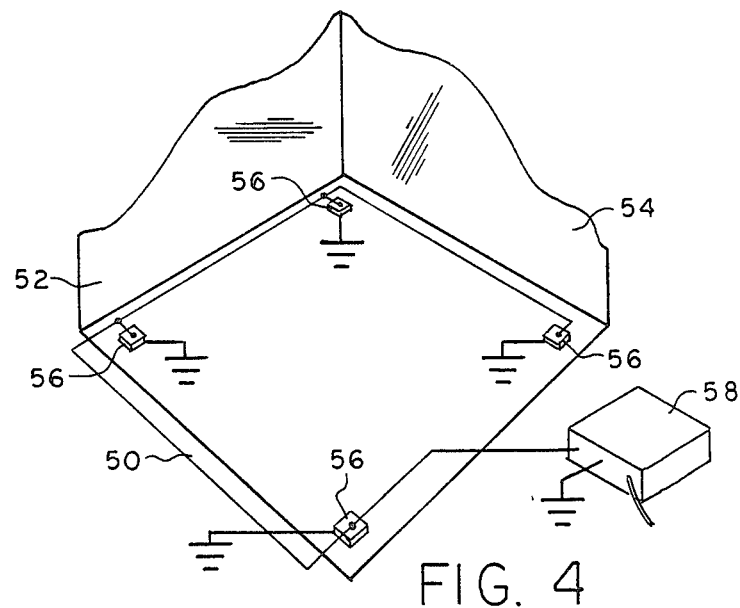
FIG. 4 is a schematic illustration of still another embodiment of the invention.

Referring to FIG. 4 there is shown in schematic form the floor 50 and two side walls 52 and 54 of a room. Four field emitters 56 are mounted on the floor near the four corners of the room and are electrically connected to a power supply 58 to apply a high frequency high voltage across each of the field emitters 56. For convenience of installation, one terminal of each of the emitters 56 is grounded and the other terminals are connected to the hot terminal of the power supply 58. The field emitters may be of the type shown in FIG. 2 or of the type shown in FIG. 3 and the power supply 58 provides an output of at least 5000 volts RMS at a frequency of at least 20 kiloHertz. By strategically locating the field emitters 56 within the room the need for fans for circulating the air through the electric fields surrounding the emitters can be eliminated thereby reducing the initial cost and the operating cost of the system as well as the noise associated with such fans.

In order to substantiate the fact that doping of the insulator with different non-dielectric materials alters the resultant field and in some cases increases the field strength a substantial amount, several different experiments were conducted. In making these experiments, three different emitters of identical size and shape were constructed. The dielectric slabs were circular being 80 mm in diameter and 15 mm thick. The plates were 63 mm in diameter. In one emitter, the dielectric was a pure epoxy. In a second emitter the dielectric was epoxy containing ten percent by volume of small lead spheres dispersed throughout the epoxy so as to be insulated from one another. The spheres had a diameter of 0.7 mm. In a third emitter the epoxy was doped with silicon carbide granules having a size of 75 mesh. These granules were of the type used in lapidary grinding and thus contain a substantial amount of elemental impurities wherefor the material is actually a crude semi-conductor. It is also paramagnetic.

The emitters were connected across a high frequency power supply of 24 kV at 44 kiloHertz in the manner described in my U.S. Pat. No. 4,391,773 using a Kiethly Elecrometer and an ion/electron probe. At a distance of ten centimeters from the emitters the following measurments were made.

| Pure epoxy dielectric | $2.98 \times 10^{11}$ electrons/cm$^2$ |
|---|---|
| Epoxy with lead spheres | $3.97 \times 10^{11}$ electrons/cm$^2$ |
| Epoxy with silicon carbide | $4.76 \times 10^{11}$ electrons/cm$^2$ |

It may thus be seen that the addition of conductive or semiconducive or paramagnetic particles to the dielectric greatly increases the field strength of the field generated by the emitter.

While the present invention has been described in connection with particular embodiments thereof, it will be understood by those skilled in the art that many changes and modifications may be made without departing from the true spirit and scope of the present invention. Therefore, it is intended by the appended claims to cover all such changes and modifications which come within the true spirit and scope of this invention.

What is claimed:

1. Apparatus for generating an electric field of the type comprising a solid dielectric member sandwiched between first and second electrodes and a high voltage, high frequency energy source connected between said electrodes, the improvement wherein said dielectric member comprises,
    a dielectric material having a plurality of discrete, conductive members dispersed therein.

2. Apparatus according to claim 1 wherein said conductive members are semiconductive.

3. Apparatus according to claim 2 wherein said conductive members are formed of silicon carbide.

4. Apparatus according to claim 2 wherein said conductive members are silicon carbide granules randomly dispersed in said dielectric material.

5. Apparatus according to claim 4 wherein said dielectric material is parafinic.

6. Apparatus according to claim 1 wherein said conductive members are paramagnetic.

7. Apparatus according to claim 6 wherein said dielectric material is parafinic.

8. A method of purifying air, comprising the steps of:
    placing in proximity to said air a capacitor including a pair of electrodes spaced apart by a solid dielectric material in which a plurality of mutually spaced apart conductive pieces are dispersed,
    applying between said electrodes an A.C. voltage of at least 5000 volts having a frequency of at least 20 kiloHertz.

9. A method according to claim 8 wherein said capacitor is encapsulated in a solid insulating material.

10. A method according to claim 9 wherein a plurality of members selected from the group of conductive and semiconductive materials are dispersed in said insulating material.

11. A method of purifying the air in an environmental area, comprises the steps of
    placing at respectively spaced locations in said area a plurality of capacitors each having first and second spaced electrodes separated by a solid dielectric member formed of a dielectric material in which a plurality of conductive pieces are dispersed, and
    connecting between the associated ones of said first and second spaced electrodes an A.C. voltage of at least 5000 volts and having a frequency of at least 20 kiloHertz.

12. A method according to claim 11 wherein said pieces are semiconductive.

13. A method acording to claim 11 wherein said pieces are paramagnetic.

* * * * *